(12) United States Patent
Poye et al.

(10) Patent No.: US 6,440,365 B1
(45) Date of Patent: Aug. 27, 2002

(54) METHOD OF TREATING A BUILDING CONTAMINATED WITH BLACK MOLD

(76) Inventors: Larry J. Poye, 3440 Cypress St., Sacramento, CA (US) 95838; Stan S. Buchanan, 5829 Topp Ct., Carmichael, CA (US) 95608

(*) Notice: Subject to any disclaimer, the term of this patent is extended or adjusted under 35 U.S.C. 154(b) by 0 days.

(21) Appl. No.: 09/903,301

(22) Filed: Jul. 10, 2001

(51) Int. Cl.[7] .................................................. A61L 2/08

(52) U.S. Cl. .............................. 422/37; 422/26; 422/38

(58) Field of Search ............................. 422/26, 37, 38, 422/1

(56) References Cited

U.S. PATENT DOCUMENTS 5,567,247 A * 10/1996 Hawes et al. .................. 134/36
6,187,263 B1 * 2/2001 Nielson ........................ 422/26

* cited by examiner

*Primary Examiner*—Robert J. Warden, Sr.
*Assistant Examiner*—Sean E. Conley
(74) *Attorney, Agent, or Firm*—Thomas R. Lampe

(57) ABSTRACT

A method of treating a building contaminated with Stachybotris includes inspecting the building to identify locations in the building contaminated by the Stachybotris, applying a treatment liquid to the Stachybotris at the locations, the treatment liquid including hydrochloric acid, and heating the treatment liquid for a length of time after it has been applied to the Stachybotris.

11 Claims, 1 Drawing Sheet

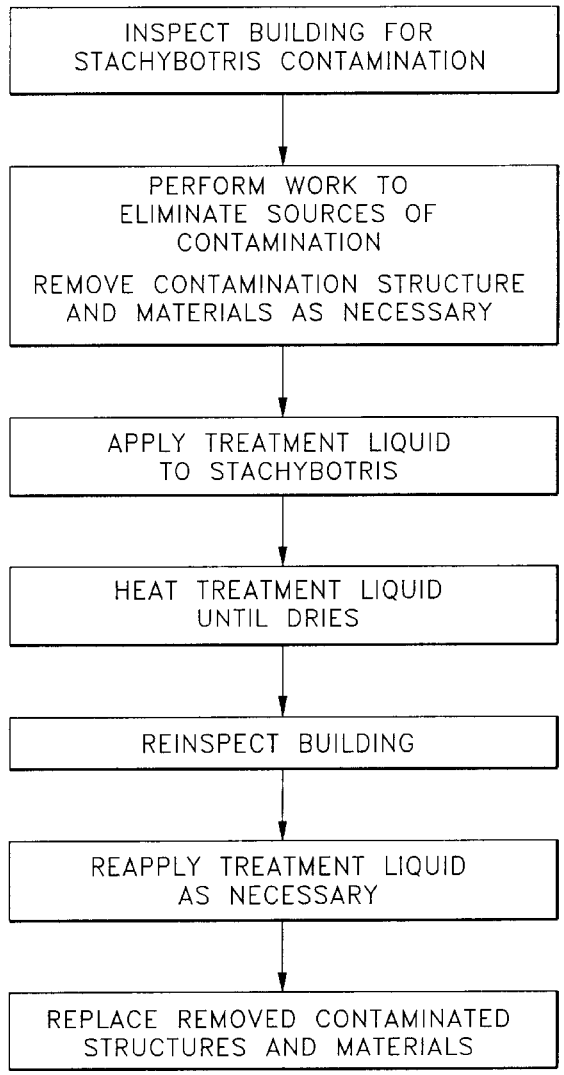

```
┌─────────────────────────────┐
│    INSPECT BUILDING FOR     │
│   STACHYBOTRIS CONTAMINATION │
└─────────────────────────────┘
              │
              ▼
┌─────────────────────────────┐
│       PERFORM WORK TO       │
│     ELIMINATE SOURCES OF    │
│        CONTAMINATION        │
│  REMOVE CONTAMINATION STRUCTURE │
│   AND MATERIALS AS NECESSARY │
└─────────────────────────────┘
              │
              ▼
┌─────────────────────────────┐
│     APPLY TREATMENT LIQUID  │
│       TO STACHYBOTRIS       │
└─────────────────────────────┘
              │
              ▼
┌─────────────────────────────┐
│     HEAT TREATMENT LIQUID   │
│         UNTIL DRIES         │
└─────────────────────────────┘
              │
              ▼
┌─────────────────────────────┐
│      REINSPECT BUILDING     │
└─────────────────────────────┘
              │
              ▼
┌─────────────────────────────┐
│    REAPPLY TREATMENT LIQUID │
│         AS NECESSARY        │
└─────────────────────────────┘
              │
              ▼
┌─────────────────────────────┐
│  REPLACE REMOVED CONTAMINATED │
│    STRUCTURES AND MATERIALS │
└─────────────────────────────┘
```

*Fig. 1*

METHOD OF TREATING A BUILDING CONTAMINATED WITH BLACK MOLD

TECHNICAL FIELD

This invention relates to a method of treating a building contaminated with Stachybotris, for example, Stachybotris chartarum, commonly called black mold or stachy.

BACKGROUND OF THE INVENTION

Stachybotris, for example Stachybotris chartarum, is invading a good many buildings and homes. The mold isn't new, nor is the problem; but recent outbreaks have caused people to go to extremes to deal with it.

Air quality experts and doctors link the mold to illnesses ranging from dry coughs and runny noses to oozing rashes and constant fatigue.

Getting rid of the mold is a problem and, thus far, truly effective approaches for doing this have not been developed. Despite all the mold and mildew removers for sale in supermarkets, they are relatively ineffective in ridding a residence or other building of Stachybotris.

Scrubbing of the mold can release spores into the air to spread to furniture and clothing. Left untreated, black mold can contaminate a whole house. Victims have spent thousands of dollars trying to rid their apartments or houses of the menace, throwing out treasures and even burning down their residences in an attempt to be free of the mold. One of the problems is that black mold often reoccurs even when existing treatments for mold removal are tried.

While black mold can occur at many locations in a building, sheet rock and ceilings are particular culprits in this battle because they contain organic materials that, when wet, provide a constant food source for mold.

DISCLOSURE OF INVENTION

The present invention relates to a method which efficiently and effectively eliminates the black mold organism. Recurrence of black mold is highly unlikely when the method of this invention is practiced.

The present invention relates to a method of treating a building contaminated with Stachybotris which includes the step of inspecting the building to identify locations in the building contaminated with Stachybotris.

The method also includes the step of applying a treatment liquid to the Stachybotris at said locations.

The treatment liquid is formulated to include hydrochloric acid and water and the ratio of water to hydrochloric acid in the treatment liquid by volume falls within the range of from about 4 to 1 to about 1 to 1.

After the treatment liquid has been applied, it is heated for a length of time to destroy the Stachybotris.

Other features, advantages and objects of the present invention will become apparent with reference to the following description and accompanying drawings.

BRIEF DESCRIPTION OF DRAWINGS

FIG. 1 is a schematic block diagram illustrating steps of the method of this invention.

MODES FOR CARRYING OUT THE INVENTION

Referring now to the drawing, the first step of the method of the present invention is to inspect a building for Stachybotris contamination. For example, evidence of contamination may be found at locations in sheet rock, ceiling areas, floor tile, ceramic or vinyl flooring or numerous other areas of a house.

After the locations of contamination have been found, remediation steps are conducted by a visual and thorough inspection of contaminated areas to isolate the causation of the water intrusion which has caused the contamination. For example, a roof inspection may find improperly installed or missing roof components. The roof edge metal flashing, for example, may not be installed properly or inferior felt or tar paper may have been used. These problems are addressed and the source of water intrusion fixed before proceeding with the rest of the method steps.

The areas to be decontaminated should be vacated by occupants for a minimum of forty eight hours. After this has been done, a particular treatment liquid is applied to the locations of contamination. In particular, the treatment liquid includes water and hydrochloric acid, the ratio of water to the hydrochloric acid by volume falling within the range of from about four to one to about one to one.

It will be appreciated that the treatment liquid also will be applied to the area surrounding the detected locations of contamination, including any areas situated between the contamination and the location of water intrusion.

For example, the treatment liquid may be injected through one half inch-one inch access pathways into fiberglass insulation to permeate mold-infected areas from the top of the ceiling area down to the floor base area. Plastic sheets may be secured in place to cover carpet areas not affected by the mold. Conventional sprayers may be utilized to spray the affected surfaces and soak into or permeate building structures such as frames and materials.

After application of the desired amount of treatment liquid at the desired locations, heat is applied to the mold and liquid. This suitably may be accomplished by use of a mobile heat source that is capable of generating 80 degrees to 100 degrees Fahrenheit, it having been found that a temperature of about 80 degrees is the minimum required to effectively carry out the present method. A fan is preferably associated with the heater to circulate the air. Ambient heat reaching such levels can be used, and only a fan employed. In any event 80 degrees is the desired minimum temperature.

This treatment will result in destruction of the black mold. While the precise manner in which this occurs is not known for certain, hydrochloric acid is particularly destructive to cellulose, breaking the cellulose chain into smaller units, resulting ultimately in complete hydrolysis. It is believed that the hydrochloric acid portion of the treatment liquid when applied to surface areas contaminated by mold chemically causes electron exchange by bombarding the mold organisms, breaking the cellulose chain into smaller units, resulting ultimately in hydrolysis. In any event, utilization of the treatment liquid described above and heating thereof results in conversion of the mold to a harmless black powder which can readily be removed. After an eight hour hydrolysis period, a second application of treatment liquid may be applied which includes a white pigmented water-base primer delivered by a spray mist to function as a stain blocker. Also, if desired, a scent producing ingredient such as an orange oil extract may be utilized.

Reinspection of the premises, specifically of the areas treated, may call for further application of the treatment liquid and the heating and drying thereof as described above.

Technicians performing the method stated above shall, of course, wear suitable protective equipment such as respiratory equipment, gloves, safety goggles, and protectant suits head to toe. As indicated above, it is desired that the premises remain vacant by occupants for at least forty eight hours.

In some situations, the mold organism may have caused irreparable damage to building materials and structures such as gypsum wallboard, sheet rock and ceiling areas, carpet, window sills, bathroom walls and ceilings. In such situations, it is required to remove the damaged materials and structural support component prior to application of the treatment fluid. For example, entire sections of sheet rock which have lost their structural integrity may be removed and subsequently replaced after the liquid treatment, heating and drying steps indicated above.

It is known to have Stachybotris contamination of concrete flooring and a slab may show signs of mold growth that will lead to contamination of wallboard, sheet rock and studs. With this form of contamination it may be necessary to jack hammer out and properly repour a slab. Subject to the level of contamination, a concrete sealer can be applied.

The principles of the present may also be utilized to treat contamination of an HVAC ventilation system. The duct work may be scanned by a remote video camera to identify locations of contamination.

After this has been done, the HVAC system must be shut down for a forty eight hour period with vent duct openings sealed, for example by plastic sheets.

The ventilation access area is opened and a heavy mist of treatment liquid is sprayed with a pressure washer throughout the entire vent duct area.

After the minimum eight hour hydrolysis cycle has passed, a mobile heating source providing a minimum heating of 80 degrees Fahrenheit is aimed into the vent duct. A fan is employed to blow air through the system for the eight hour minimum hydrolysis time frame. A video camera can be sent down the duct to reinspect for hydrolysis.

The following are examples of various inspection and remediation levels employed when practicing the teachings of the present invention. These examples are illustrative only and are not to be considered exhaustive of the approaches to be followed when practicing the present invention.

Inspection Level 1

Interior

Inspect walls, ceilings, counter-top area, water closets under sinks, water heater closets. Inspect high ceiling corners adjacent to windows. Inspect door and slider door areas where sheet rock shows water damage. Look for window sills where moisture build-up indicates mold culture. Check wash room areas.

Exterior

Inspect rooftop for deteriorated felt, brittle or cracked shingles and no presence of galvanized 2" drip edge flashing. Pull fascia boards along windows. Check for mold contamination where water intrusion is apparent. Inspect eaves. (Applicable to Levels I–IV).

Remediation Level 1

Interior

Cover carpet with 1MM plastic covering, tape to baseboards under areas designated for treatment. Drill ¾" access holes between studs using electronic stud finder, top access hole 6" from ceiling, second access hole 48" up from baseboard. Space two access holes every 16" between stud areas. Spray treatment liquid into pre-drilled holes at five second intervals five times. Allow solution to permeate insulation for eight hours. Mold will terminate behind interior walls. Apply second treatment by adding a pigmented stain blocker behind walls and spray treatment liquid with stain blocker onto interior walls. Use 80000 BTU propane heater at a minimum setting at 100 degrees F. for two hours. Ultimate and complete hydrolysis is achieved.

Liquid Treatment Mixture—Level 1

Mixture of four gallons water to one gallon hydrochloric acid/one cup of oil based detergent to provide scent—add 1 quart of pigmented stain blocker. Treats 600 Sq. Ft.

Inspection Level II

Inspect walls, ceilings and counter-top area, water closet areas under sinks, water heater closets, ceiling and wall areas in corners near single pane windows. Lift carpets where mold growth caused by water intrusion in entry door areas including glass sliding door areas. Remove sheet rock center on center on studs, check for and remove damaged sheet rock from door entry areas, slider door areas, and expose studs. Inspect attic area if applicable and roof area for water intrusion. Lift carpets to check for mold contamination. (Same steps as in Level 1 Re: Roofing).

Remediation Level II

Cover carpet with 1MM plastic covering, tape to baseboards under areas designated for treatment. Drill ¾" access holes between studs using electronic stud finder, (same steps as in Level I).

Remove damaged or deteriorated sheet rock. Drill access holes 6" down from ceiling, second access holes 48 inches up from baseboard. Spray treatment liquid into pre-drilled holes at five second intervals. Allow eight hours for solution to permeate insulation. Spray all studs contaminated by mold. Seal areas not contaminated with plastic, covering entry areas, and areas not to be treated. Use 80000 BTU propane heater for two hours at a minimum degree of 100 degrees F. to complete ultimate hydrolysis.

Liquid Treatment Mixture—Level II

Mixture—four gallons water, one gallon hydrochloric acid, one cup oil based detergent—add one quart pigmented stain blocker. Four gallons treats 1200 Sq. Ft.

Inspection Level III

Interior

Pull and remove carpet from slab floor where mold contamination is apparent, mold growth caused by water intrusion from concrete. Check if mold contamination is extensive throughout structure. Remove all carpet in sections and seal in plastic sheet until reinstalled. (Same steps as in Levels I and II). Inspect concrete slab for high areas of moisture evident by mold cultures. Cut sheet rock at bottom of stem walls where it is visible in dry wall areas connected to stem walls and studs (Same steps as in Levels I and II).

Remediation Level III

Interior

Expose stem wall and all studs and top and bottom plates contaminated by water intrusion from concrete slab. (Same steps as Levels I and II). Spray slab with treatment liquid, also studs and all areas where apparent mold growth is prevalent. Drill access holes as in Level II and spray in between walls. Allow eight hours to dry or use portable heat source for two hours. Pull carpet up around door areas, entry and washroom area for liquid treatment. Use 80000 BTU heat source such as a propane heater. Control heat levels a minimum of two hours.

Liquid Treatment Mixture—Level III

Mixture—eight gallons water/two gallons hydrochloric acid, two cups of oil based detergent, add two quarts of a pigmented stain blocker. Eight gallons treats 2400 Sq. Ft. (Includes concrete slab) use a concrete sealer after hydrolysis achieved.

Inspection Level IV

Interior

Multi-family units—Apartment units

Inspect wall areas, ceilings, bathrooms, and window sills especially where single pane windows exist. If during the fall months examine location of moisture build-up in these areas. Check for drip edge flashing. Lower level units require inspection of areas under carpet adjacent to door ways, entry areas, and stem wall areas. Any indication of mold or smell of mold growth in carpets requires inspection of cement slab for signs of mold culture growing from areas below slab. Same remediation steps as indicated in Levels I—III. Inspect dry wall area around HVAC ducts. Ventilation ducts in multi-family units are connected for central heat and for central air. When available utilize fiber optic camera to inspect interior of vent ducts. Inspect concrete slab areas in lower level units, any indication of mold growth in slab requires application of treatment liquid.

Liquid Treatment Mixture—Level IV

Average apartment unit square footage 600 sq. ft. Level I–II contamination determined by each unit where mold culture is visible in moisture intrusion areas; two gallons water/one gallon hydrochloric acid/four ounces oil based detergent/add one quart pigmented stain blocker. Level III decontamination steps as indicated above, however, determined by per unit treatment requirement as needed to terminate mold culture. Four gallons water/two gallons hydrochloric acid, four ounces oil based detergent/add one quart pigmented stain blocker.

Remediation Steps

Any building material or structural building components contaminated by mold is to be carried away in thirty six gallon heavy duty contractor bags with wire ties. This especially applies to dry wall that has disintegrated due to continuous water intrusion. In the event the sheet rock has not crumbled or water damage is not evident, treat walls as in Level II. (Require apartment owner to call roofing inspector for roof inspection to identify water intrusion problems).

The Invention claimed is:

1. A method of treating the interior of a building contaminated with Stachybotris chartarum, said method comprising the steps of:

inspecting the building to identify locations in the interior of the building contaminated with Stachybotris chartarum;

applying a treatment liquid to the Stachybotris chartarum at said locations in the interior of the building, said treatment liquid including water and hydrochloric acid, the ratio of water to hydrochloric acid by volume falling within the range of from about four to one to about one to one;

heating the interior of the building at said locations to heat the treatment liquid at said locations to a temperature of at least 80 degrees Fahrenheit after the treatment liquid has been applied to the Stachybotris chartarum; and substantially continuously maintaining the temperature at said locations at at least 80 degrees Fahrenheit for at least eight hours to dry the treatment liquid at said locations.

2. The method according to claim 1 wherein said treatment liquid is formulated to additionally include a stain blocking agent.

3. The method according to claim 1 including the step of eliminating one or more sources of Stachybotris contamination after the step of inspecting the building and prior to the step of applying treatment liquid.

4. The method according to claim 1 including the step of removing selected structures and materials contaminated with Stachybotris from said locations after the step of inspecting the building and prior to the step of applying treatment liquid.

5. The method according to claim 1 including the step of causing air flow at said locations during the step of heating the treatment liquid.

6. The method according to claim 1 wherein said step of applying treatment liquid to the Stachybotris at said locations comprises spraying said treatment liquid on surfaces of structures and materials contaminated with the Stachybotris.

7. The method according to claim 1 wherein said step of applying treatment liquid to the Stachybotris chartarum at said locations comprises saturating structures and materials contaminated with the Stachybotris chartarum with said treatment liquid.

8. The method according to claim 1 wherein said step of applying treatment liquid to the Stachybotris comprises injecting structures and materials contaminated with the Stachybotris with said treatment liquid.

9. The method according to claim 1 wherein said step of applying a treatment liquid includes forming holes in walls in said building and injecting said treatment liquid through said holes to framing of said building.

10. The method according to claim 1 wherein the treatment liquid is formulated to additionally include a predetermined source of scent.

11. The method according to claim 8 including the step of replacing removed contaminated structures and materials with uncontaminated structures and materials after the step of heating the treatment liquid.

* * * * *